United States Patent [19]

Magolan

[11] 3,954,978
[45] May 4, 1976

[54] LINIMENT

[76] Inventor: Angeline R. Magolan, 1452 Elm St., Wyandotte, Mich. 48192

[22] Filed: Mar. 3, 1975

[21] Appl. No.: 554,973

Related U.S. Application Data

[63] Continuation-in-part of Ser. No. 447,979, April 4, 1974, abandoned.

[52] U.S. Cl. .............................................. 424/195
[51] Int. Cl.$^2$ ......................................... A61K 35/78
[58] Field of Search .................................... 424/195

[56] References Cited
UNITED STATES PATENTS

| | | | |
|---|---|---|---|
| 104,758 | 6/1870 | Myers ................................ | 424/230 |
| 155,556 | 3/1874 | Van Geasen ....................... | 424/230 |

OTHER PUBLICATIONS

Chemical Abstracts: Vol. 16:3109$^8$; Vol. 23:3005$^9$; Vol. 45:8599g; Vol. 58:13711c & Vol. 73:42378g, (1970).

Lyons, "Plant Names Scientific & Popular," (p. 77), 1900, Published by Nelson, Baker & Co.

*Primary Examiner*—Donald B. Moyer
*Attorney, Agent, or Firm*—McGlynn and Milton

[57] ABSTRACT

A method of relieving pain by topically applying effective amounts of a pain relieving composition comprising isopropyl alcohol and an active extract of the roots of a plant selected from the group consisting of bluebell, harebell and bellflower. The extract is prepared by soaking cut up roots in isopropyl alcohol in a glass container for 1 year and straining the mixture of roots and alcohol to obtain the extract. Preferably, the soaking mixture contains a ratio of approximately 80 fluid ounces of isopropyl alcohol to 2½ pounds of chopped up roots.

2 Claims, No Drawings

LINIMENT

This application is a continuation-in-part of applicant's co-pending application Ser. No. 447,979, filed Apr. 4, 1974 and now abandoned.

This invention relates to a liniment and the method for making the liniment, which liniment may be utilized for the temporary relief of aches and pains resulting from arthritis.

The liniment is produced by cutting up the fresh roots from one of a group of plants consisting of bluebell, harebell and bellflower. Fresh roots are those which have been freshly removed from the growing environment. The fresh cut-up roots are soaked in isopropyl alcohol $(CH_3)_2CHOH$, in a glass container for a minimum of 1 year. Preferably, the mixture contains a ratio of about 80 fluid ounces of isopropyl alcohol to 2½ pounds of chopped up roots.

After aging, the resulting extract, that is, the isopropyl alcohol and the matter derived from the cut-up roots is strained to separate the liquid extract from the roots. The resulting extract is then mixed with additional isopropyl alcohol and oil of wintergreen. The oil of wintergreen, or gaultheria oil, is a commonly known compound which is derived from the leaves of *Gaultheria procumbens*, a small evergreen plant. In preparation, 61 fluid ounces of the extract is combined with 62 ounces of fresh isopropyl alcohol and about 5 ounces of oil of wintergreen.

The liniment is then ready for use. The liniment is applied to the skin adjacent the joints of a human being by applying the liniment and rubbing the liniment into the skin.

In one example, an arthritic woman having arthritis in her hands and arms had the liniment applied to her hands and arms and rubbed thereinto daily and gained more relief than obtained by the same procedure using merely alcohol.

It has been known to use alcohol in various combinations for relieving pain; however, it has been found that the specific combination of an extract resulting from the soaking of chopped-up roots of one of bluebell, harebell or bellflower with isopropyl alcohol for a minimum of a year and additional isopropyl alcohol and wintergreen when applied to arthritic joints by rubbing onto the skin adjacent the joints has been found by users to provide unexpected relief from arthritic pain.

The invention has been described in an illustrative manner, and it is to be understood that the terminology which has been used is intended to be in the nature of words of description rather than of limitation.

Obviously, many modifications and variations of the present invention was possible in light of the above teachings. It is, therefore, to be understood that within the scope of the appended claims, the invention may be practiced otherwise than as specifically described.

The embodiments of the invention in which an exclusive property or privilege is claimed are defined as follows:

1. A method of relieving pain by topically applying effective amounts of a pain relieving composition comprising an active extract of the roots of a plant selected from the group consisting of bluebell, harebell and bellflower, said extract being prepared by soaking cut up roots in isopropyl alcohol in a glass container for 1 year and straining the mixture of roots and alcohol to obtain the extract.

2. The method of claim 1 wherein the mixture contains a ratio of approximately 80 fluid ounces of isopropyl alcohol to 2½ pounds of chopped up roots.

* * * * *